(12) United States Patent
Bozic

(10) Patent No.: US 10,364,808 B2
(45) Date of Patent: Jul. 30, 2019

(54) PUMPING SYSTEM FOR CHROMATOGRAPHY APPLICATIONS

(71) Applicant: SANOFI-AVENTIS DEUTSCHLAND GMBH, Frankfurt am Main (DE)

(72) Inventor: Alexander Bozic, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 173 days.

(21) Appl. No.: 15/116,971

(22) PCT Filed: Feb. 13, 2015

(86) PCT No.: PCT/EP2015/053058
§ 371 (c)(1),
(2) Date: Aug. 5, 2016

(87) PCT Pub. No.: WO2015/121402
PCT Pub. Date: Aug. 20, 2015

(65) Prior Publication Data
US 2017/0167476 A1   Jun. 15, 2017

(30) Foreign Application Priority Data
Feb. 17, 2014 (EP) .................... 14155323

(51) Int. Cl.
*F04B 11/00* (2006.01)
*F04B 23/06* (2006.01)
(Continued)

(52) U.S. Cl.
CPC ............ *F04B 23/06* (2013.01); *F04B 11/005* (2013.01); *F04B 49/065* (2013.01); *F04B 49/08* (2013.01);
(Continued)

(58) Field of Classification Search
CPC ........... F04B 23/06; F04B 23/04–23/14; F04B 49/08; G01N 30/32; G01N 2030/326
See application file for complete search history.

(56) References Cited

U.S. PATENT DOCUMENTS

| 8,215,922 B2 | 7/2012 | Berger et al. |
| 2005/0095145 A1 | 5/2005 | Hiraku et al. |

(Continued)

FOREIGN PATENT DOCUMENTS

| JP | H11-133011 | 5/1999 |
| JP | 2006-292392 | 10/2006 |
| JP | 2012-32187 | 2/2012 |

OTHER PUBLICATIONS

International Preliminary Report on Patentability in International Application No. PCT/EP2015/053058, dated Aug. 23, 2016, 6 pages.

(Continued)

*Primary Examiner* — Paul M. West
(74) *Attorney, Agent, or Firm* — Fish & Richardson P.C.

(57) ABSTRACT

A pumping system for compressible fluids comprises a first pump having a first pump outlet and a second pump having a second pump outlet. The first pump outlet and the second pump outlet merge in a junction which is in fluid communication with a main outlet. The pumping system further comprises a control to regulate the output pressure of the second pump on the basis of a measurement of the output pressure of the first pump. The corresponding method of operating a pumping system is also disclosed.

19 Claims, 3 Drawing Sheets

(51) Int. Cl.
*F04B 49/06* (2006.01)
*F04B 49/08* (2006.01)
*G01N 30/32* (2006.01)

(52) U.S. Cl.
CPC .......... *G01N 30/32* (2013.01); *F04B 2205/05* (2013.01); *F04B 2205/13* (2013.01)

(56) References Cited

U.S. PATENT DOCUMENTS

| | | |
|---|---|---|
| 2010/0202897 A1 | 8/2010 | Corral et al. |
| 2013/0104631 A1 | 5/2013 | Tokuo et al. |

OTHER PUBLICATIONS

International Search Report and Written Opinion in International Application No. PCT/EP2015/053058, dated May 27, 2015, 9 pages.

PUMPING SYSTEM FOR CHROMATOGRAPHY APPLICATIONS

CROSS-REFERENCE TO RELATED APPLICATIONS

This application is a U.S. national stage application under 35 USC § 371 of International Application No. PCT/EP2015/053058, filed on Feb. 13, 2015, which claims priority to European Patent Application No. 14155323.0, filed on Feb. 17, 2014, the entire contents of which are incorporated herein by reference.

TECHNICAL FIELD

The present disclosure relates to the pumping systems for chromatography applications, in particular for high-performance liquid chromatography (HPLC) or super critical fluid chromatography (SFC). The disclosure further relates to a chromatography system and to a method of operating a pumping system for chromatography systems.

BACKGROUND

Super critical fluid chromatography allows to separate a component, i.e. an extractant from another component, i.e. a matrix, by making use of a super critical fluid as the extracting solvent. By means of SFC and HPLC, various substances can be chemically analyzed, identified and quantified. Making use of carbon dioxide as a super critical fluid in SFC applications, the extraction of the substances has to be conducted under super critical conditions. Regarding carbon dioxide as the super critical fluid of choice, the extraction has to be conducted above the critical temperature of 31° C. and above a critical pressure of 74 bar.

For keeping $CO_2$ or a $CO_2$-mixture in a liquid state inside a chromatography column, the entire chromatography system has to be kept on a predefined pressure level. For this purpose, downstream of the chromatography column and downstream of a respective detector, a back-pressure regulator is typically provided, to keep the pressure inside the chromatography system on a predefined level. Upstream of the chromatography column there is typically provided a preparation stage comprising at least one pump in order to pressurize the at least one solvent.

With HPLC or SFC chromatography applications the solvents, such like ethanol and/or $CO_2$ have to be pressurized up to a level of several hundred bar, typically up to 400 bar, as high as 1000 bar or even above. In these pressure ranges solvents like $CO_2$ typically exhibit a comparatively large compressibility. When making use of conventional pumps, such like reciprocating pumps, feed flow pulsations are typically observable in the fluid flow at a pump's outlet.

In FIG. 2 a conventional pump 20 in form of a duplex pump with two pump heads 22, 24 is schematically illustrated. In a chromatography environment, such like in an SFC system, the inlet 26 of the pump 20 is connected to a cooler 12 which is in fluid communication with a storage reservoir 102 being at least partially filled with a solvent, e.g. liquid $CO_2$. By means of the cooler 12 the liquid solvent can be pre-cooled to a well-defined process temperature. The reciprocating pump 20 with its two pump heads 22, 24 is further equipped with numerous check valves 23, 25 downstream and upstream of the pump heads 22, 24 which are arranged in parallel between the inlet 26 and the pump's outlet 21.

In operation, each pump head 22, 24 makes use of a piston which is driven by a cam that alternately aspirates fluid from the inlet 26 by increasing the available pump head volume, then dispenses the fluid to the outlet 21 by decreasing this volume. The flow direction is controlled by the check valves 23, 25 that isolate the pump heads 22, 24 from the output pressure during aspiration and from the input pressure during dispensing. Even though FIG. 2 illustrates a duplex type arrangement of a pump 20 other geometries, hence a simplex pump with only one pump head or triplex or quad pumps with three and four pump heads are also generally applicable for chromatography applications.

The pulsations of the fluid flow over time arising at the output 21 of the pump 20 are schematically illustrated in FIG. 3. As can be seen from the diagram 60 the flow rate and hence a flow volume of the pressurized liquid over time at the outlet 21 of the pump 20 may drop down to about 5% of the maximum flow rate as illustrated by various flow rate drops 61 of the diagram according to FIG. 3. These inevitable variations or pulsations of the fluid flow limit the precision of the chromatography system.

In document U.S. Pat. No. 8,215,922 B2 this problem is identified. There, a pressurized pumping system is described that comprises a first pump that operates to increase the pressure of a fluid and that comprises a second pump, connected in series to the first pump, wherein the second pump receives the pressurized fluid from the first pump and meters the fluid to an output of the second pump. An input pressure of the fluid that is received by the second pump from the first pump is held near to or slightly below the output pressure of the fluid at the output of the second pump such that a minimal density change occurs to the fluid traveling between the input and output of the second pump.

Connecting two pumps in series requires that both pumps have to provide a comparatively large flow volume. Moreover, with this approach it is in particular the pumping speed of a booster pump that needs to be controlled, which may be rather costly and elaborate.

SUMMARY

In some aspects, a pumping system for compressible fluids, in particular, for chromatography applications, is operable to reduce or to eliminate feed flow pulsations in the outlet stream of the pumping system. The pumping system may have a rather simple structure and be easily controllable. Moreover, in certain aspects, a pumping system is retrofittable to existing pumping systems for chromatography applications.

In a first aspect a pumping system for compressible fluids, in particular for solvents for chromatography applications, such like $CO_2$ is suggested. The pumping system comprises a first pump having a first pump outlet. The pumping system further comprises a second pump having a second pump outlet. The first pump outlet and the second pump outlet merge in a junction which is in fluid communication with a main outlet of the pumping system. In other words, downstream of the junction there is provided a main outlet which due to the junction is in fluid communication with the first pump outlet and with the second pump outlet.

In this way a fluid flow emanating from the first pump outlet and a fluid flow emanating from the second pump outlet merge in the junction and are fed further downstream to or through the pumping system's main outlet.

Furthermore, the pumping system comprises a control to regulate a second pump's second output pressure p2 on the basis of a measurement of the first pump's first output pressure p1. First and second output pressures p1 and p2 nominate the output pressure of the second pump and of the first pump, respectively. Moreover, the first pump outlet is the only outlet of the first pump while the second pump outlet is the only outlet of the second pump. Typically, each one of first and second pumps comprises one outlet, designated as first or second pump outlet, respectively.

Since the control is operable to regulate the second pump's output pressure p2 on the basis of a measurement of the first pump's output pressure p1 a pressure controlled regulation of the second pump is provided by way of which feed flow pulsations in the output stream of the first pump's outlet can be effectively compensated or at least reduced by means of the second pump. Here, the second pump is dimensioned and designed to provide a reduced flow rate compared to the flow rate or flow volume of the first pump. The second pump is particularly operable to provide an auxiliary fluid flow at such particular points of time where pressure drops or flow rate drops of the fluid flow of the first pump's outlet occur.

The control is particularly adapted to regulate the second pump's second output pressure to counteract and to prevent that the total pressure and flow rate downstream of the junction exceeds a predefined level. Regulation and/or control of the second pump's output pressure therefore serves to keep the flow volume downstream of the junction within predefined margins or levels, typically below a predefined and constant flow volume required by the chromatography application downstream of the main outlet.

While the first pump typically serves and acts as a main or booster pump the second pump may act and serve as an auxiliary or dosing pump which is exclusively adapted and designed to compensate the first pump's feed flow pulsations, i.e. frequently occurring pressure drops or feed flow drops in the outlet of the first pump.

Measuring and regulating of first and/or second pump's output pressure particularly means to regulate and/or to measure the pressure of the respective pressurized fluid flowing in the respective outlet of first and/or second pump.

Since the second pump particularly serves to compensate feed flow pulsations of the first pump outlet the maximum flow volume of the second pump does not have to be as large as the maximum flow volume of the first pump. Consequently, the dimensions of the second pump can be much smaller compared to those of the first pump. In effect, a cost expenditure for the second pump can be kept significantly smaller compared to the monetary investment of the first pump. In this way, the pumping system can be kept rather compact and cost efficient. Moreover, the first pump may be represented by a pump of an installed chromatography system. By appending and coupling of the second pump to the first pump together with the junction and the control, also existing pumping systems can be retrofitted with the second pump to provide a pumping system according to certain embodiments of the present invention.

According to a further embodiment at least one check valve is arranged between the junction and the second pump outlet. By means of the check valve a fluid flow from the first pump outlet towards the second pump outlet can be effectively prevented. Typically, the check valve opens when the pressure in the first pump outlet drops below a pressure level of the second pump outlet. This is typically the case, when a pressure drop 61 as illustrated in FIG. 3 occurs, which is typically linked with a corresponding drop of the fluid flow in the first pump outlet.

By means of the junction of the first and second pump outlet the fluid flow in the main outlet can be kept at a rather constant and pressure-dropless level since any pressure drops or fluid flow drops occurring in the first pump outlet can be compensated by the supplemental and compensating fluid flow of the second pump outlet. Here, the check valve between the junction and the second pump outlet is implementable in many different ways in order to provide a substantially delayless operation. In this way and by means of the check valve a pressure drop or a drop of the fluid flow in the first pump outlet can be almost instantly compensated by the fluid flow provided by the second pump in the second pump outlet.

According to another embodiment the first pump comprises a first pump inlet. Also the second pump comprises a second pump inlet. Both, first and second pump inlets are connectable in parallel with a storage reservoir which is at least partially filled with the compressible fluid. Typically first and second inlets are connectable or are actually connected with one and the same storage reservoir. Between the storage reservoir and first and second pump inlets there may be provided a cooler in order to pre-cool the compressible liquid to a predefined temperature before it is pressurized by first and/or second pumps. Since both pumps are in fluid communication with one and the same storage vessel, first and second pumps are adapted to pressurize and to feed the same type of solvent for a chromatography application.

In other words and according to another embodiment first and second pumps are arranged parallel with respect to each other. Hence, the pressurized fluid provided in the storage vessel may either flow through the first pump, through the junction and into the main outlet or it may flow via the second pump and through the junction into the main outlet. By arranging first and second pumps parallel in the fluid path between the storage reservoir and the main outlet different flow rates and different, hence cost-efficient first and second pump configurations can be realized.

According to another embodiment the control is operable to adjust the second pump's output pressure below the first pump's output pressure. As already mentioned above, any mentioning of an output pressure of a pump relates to the fluid pressure of the pressurized fluid that is pressurized by the respective pump. By adjusting the second pump's output pressure at least slightly below the first pump's output pressure any over-compensation of feed flow pulsations can be effectively prevented. By keeping the operating pressure of the second pump below the predefined output pressure of the first pump the total pressure at the main outlet may be kept below or at a predefined first pump's output pressure.

Adjusting of the second pump's output pressure is typically conducted by the control, which may be implemented by a microcontroller or by a PLC control system or similar control systems or control loops. Adjusting of the second pump's output pressure may include to temporally switch on and switch off the second pump depending on the actually measured output pressure of the first pump. If a pressure drop occurs in the stream of the pressurized fluid in the first pump outlet, such a pressure drop will be almost instantly detected. As a consequence, the second pump will be immediately activated. In this context it is to be noted that regulation or adjustment of the second output pressure may be equally attained by dynamically modifying the second pump's output pressure, e.g. by continuously raising and/or lowering the pump capacity or pump power.

As an alternative it is even conceivable, that the second pump is controlled and operated on the basis of a measurement of the second output pressure, hence of the fluid pressure inside the second pump outlet. In this way, the control may provide a rather constant pressure level in the second pump outlet. In the event that the pressure level in the first pump outlet drops below a predefined level the check valve between the junction and the second pump outlet may open, thus leading to a pressure drop in the second outlet by way of which a regulation loop of the second pump is operable to increase the flow volume of the second pump to counteract the pressure drop and to keep the fluid pressure in the second pump outlet at a predetermined constant level.

In another embodiment the control is operable to adjust the second pump's output pressure, hence the second output pressure p2 to a level which is from 1 bar to 10 bar below the first pump's output pressure p1. In the present context, the first pump's output pressure relates to a rather constant and predetermined output pressure of the first pump which is generally required by the chromatography system connected to and fed by the main outlet. In typical operation scenarios the first pump provides a pressure of several hundred bar, typically around 400 bar or even more. Then, the pressure of the second pump is adjusted and regulated to a pressure level which is 1-10 bar smaller compared to the pressure level of the first pump. By adjusting the second pump's output pressure p2 to a pressure level slightly below the pressure level of the first pump's output pressure p1 and by having arranged first and second pump outlets parallel, feed flow pulsations of the first pump can be almost completely compensated by the action of the second pump.

According to a further embodiment the pumping system comprises at least a first pressure sensor connected to the control and being in flow communication with the first pump outlet upstream of the junction. The first pressure sensor allows to measure the output pressure p1 of the first pump in or at the first pump outlet. In this way, the first output pressure p1 can be constantly monitored by the control.

In a further embodiment the pumping system also comprises at least a second pressure sensor that is connected to the control and which is in flow communication with the second pump outlet upstream of the junction. By means of the second pressure sensor, the second output pressure p2 of the second pump can be measured. A comparison of signals of first and second pressure sensors allows to determine a pressure difference between first and second pumps, hence between first and second pump outlets. The control, which is also adapted to regulate the operation of the second pump, may therefore keep the pressure difference between first and second output pressures p1-p2 within predefined margins, x2 and x1, typically between 1 bar and 10 bar.

Since the control is connected with the second pressure sensor and since the control is also connected to a drive of the second pump to control operation thereof the control, the second pressure sensor and the second pump are arranged in a control loop or form a control loop. In this way, the operation and behavior of the second pump during operation of the pumping system can be controlled in a well-defined and predetermined way, such that the flow volume and the pressure provided by the second pump trails the pressure of the first pump. In this way, the pumping system and in particular the second pump may dynamically react even to fluid flow pulsations, flow fluctuations and/or varying operation modes of the first or main pump.

In general, first and second pumps may be of equal type but do not have to be of equal type. Since the second pump effectively serves to compensate feed flow pulsations of the first pump even over a wide range of flow volumes it is conceivable, that first and/or second pumps are implemented as simplex pumps, duplex pumps, triplex pumps or quad pumps featuring 1, 2, 3 or 4 pump heads, respectively. Geometries and dimensions of first and second pumps may drastically differ. Moreover, in order to compensate feed flow pulsations it is of particular benefit, when first and second pumps are driven asynchronously.

When taken alone also the second pump may exhibit feed flow pulsations if it were driven in a continuous mode. Since its flow volume is typically smaller than the flow volume of the first pump it is of particular benefit, when feed flow pulsations of the second pump do not temporally overlap with feed flow pulsations of the first pump. In order to avoid such mutual overlapping of feed flow pulsations it is of particular benefit, where first and second pumps are driven asynchronously or independently from each other.

According to another embodiment the second pump's maximum flow volume is less than 20% or less than 15% or less than 10% of the first pump's maximum flow volume. Since the second pump only acts as a dosing or auxiliary pump and exclusively serves to compensate feed flow gaps in the fluid flow of the first pump's outlet it does not have to provide a large flow volume. Typically, the flow volume of the second pump may range between 10% and 20%, typically between 10% and 15% of the first pump's flow volume.

According to another aspect also a chromatography system is provided having at least one storage reservoir for storing and/or for preparing at least one solvent. The chromatography system further comprises a pumping system as described above. In typical embodiments the chromatography system also comprises a chromatography column and at least one detection or analyzing unit for analyzing, identifying and quantifying substances.

In a further aspect the chromatography system is designed as a super critical fluid chromatography system or as a HPLC system, wherein the pumping system thereof is operable to feed pressurized $CO_2$ or other compressible fluids such like ethanol, methanol, acetone, diethyl ether or the like solvents.

With the improved pumping system a rather constant and pulsationless flow of a solvent entering the chromatography system can be provided. In effect, measurement results of the chromatography system can be remarkably improved.

In a further aspect a conversion kit is provided by way of which a conventional pumping system of a chromatography system can be retrofitted with first and second pumps connected in parallel to a storage reservoir and to a main outlet of the pumping system in order to compensate feed flow pulsations of the first, hence of the main pump. The conversion kit at least comprises the second pump, a junction and a control. Hence, the second pump is to be arranged in a branch or in a flow path extending parallel to a flow path between the storage reservoir and the main outlet but extending through the first pump.

In addition at least one, typically two, namely first and second pressure sensors as mentioned above and which may also belong to the conversion kit are to be arranged in first and second pump outlets of first and second pumps, respectively. In addition, at least the second pump is operated and controlled by the control in order to adjust its output pressure p2 to a predefined level, which is slightly below the output pressure p1 of the first pump.

By means of a conversion kit existing pumping systems of chromatography systems, such like HPLC or SFC systems can be retrofitted in a rather cost efficient and straight forward way.

In another aspect a method of operating a pumping system as described above is provided. Said method comprises the steps of measuring a first output pressure p1 at the first pump's first pump outlet and adjusting a second output pressure at the second pump's second pump outlet on the basis of the measured first output pressure. The second output pressure p2 at the second pump outlet is adjusted and/or kept slightly below the output pressure at the first pump outlet. In this way the flow volume provided by the second pump exclusively serves to compensate frequent drops in the flow of pressurized fluid produced by the first pump. Since at least the second pump is exclusively pressure regulated and since the second output pressure p2 is at least slightly smaller than the first output pressure p1 a homogeneous and constant flow volume can be provided by first and second pumps even without an elaborate and quantitative measurement of fluid flows in the branches of the first pump, the second pump or at the main outlet.

In a further embodiment of the method the second output pressure p2 is kept below the first output pressure p1 by 1 bar to 10 bar. Typically, the output pressure level of first and second pumps is around several hundred bar, typically around 400 bar for SFC applications. However, it is even conceivable, that the level of the output pressure of first and second pumps is as high as 1000 bar. Also here, the pressure difference of output pressures p1 and p2 may range between 1 bar to 10 bar. Alternatively, it is conceivable, that the pressure difference between first and second output pressure ranges between 0.25% and 2.5% of the total pressure of p1.

It is to be mentioned that certain embodiments of the present invention equally refer to a pumping system, to a chromatography system comprising such a pumping system and to a method of operating such a pumping system or chromatography system, respectively. Any features, effects, benefits mentioned and described in connection with the pumping system equally apply to the chromatography system and to the method of operating the pumping system; and vice versa.

It will be apparent to those skilled in the art, that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following various features, aspects, benefits and application scenarios of an embodiment will be described by making reference to the drawings, in which.

DETAILED DESCRIPTION

Figure 1:
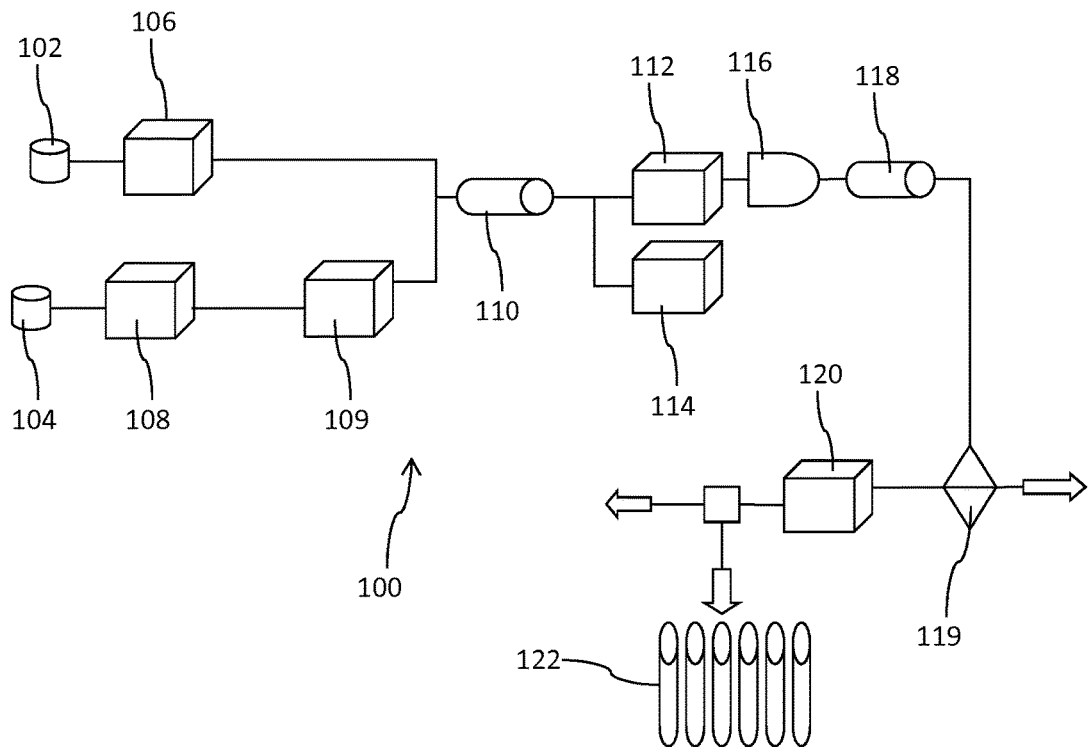
FIG. 1 schematically illustrates a chromatography system implemented as a SFC system.

The block diagram according to FIG. 1 schematically illustrates an implementation of the pumping system 10 in a super critical fluid chromatography system 100, in particular in a preparation stage 106 or 108 of such a chromatography system 100. In the illustrated embodiment the system 100 makes use of super critical $CO_2$ in addition with methanol as a solvent. As shown in FIG. 1, $CO_2$ is provided in a storage reservoir 102 and methanol is provided in a storage reservoir 104. The $CO_2$ storage reservoir 102 is in fluid connection with a preparation stage 106. The preparation stage 106 comprises a heat exchanger 12, i.e. a cooler 12 and a pumping system 10 as illustrated in FIG. 4 and as will be explained below.

In a similar way, the methanol storage reservoir 104 is in flow connection with a corresponding preparation stage 108, which typically comprises a respective pump and a heat exchanger. Downstream of the preparation stage 108 there is typically provided a probe injector 109. The $CO_2$ component and the methanol component together with the probe are then mixed and provided to a chromatography column 110. Downstream of the chromatography column 110 there is provided at least one detection or analyzing unit 112, 114.

In the illustrated block diagram, a UV-detector 112 and a mass spectrometer 114 are provided. Downstream of the UV-detector 112 there is further provided a back-pressure regulator 116 and a heat exchanger 118. The aerosol leaving the heat exchanger 118 is provided to a gas-liquid separator 119. While the $CO_2$ component is released to the environment, the methanol component is collected in a fraction collector 120. The collected fractions can be automatically collected as main fractions 122 while excess methanol may become subject to disposal.

Figure 2:
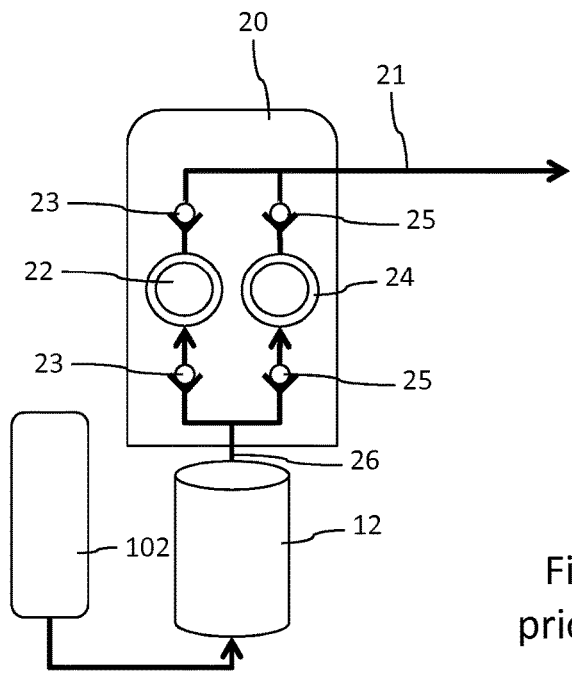
FIG. 2 shows a preparation stage of an SFC system with a conventional pump according to the prior art.
Figures 3, 4:
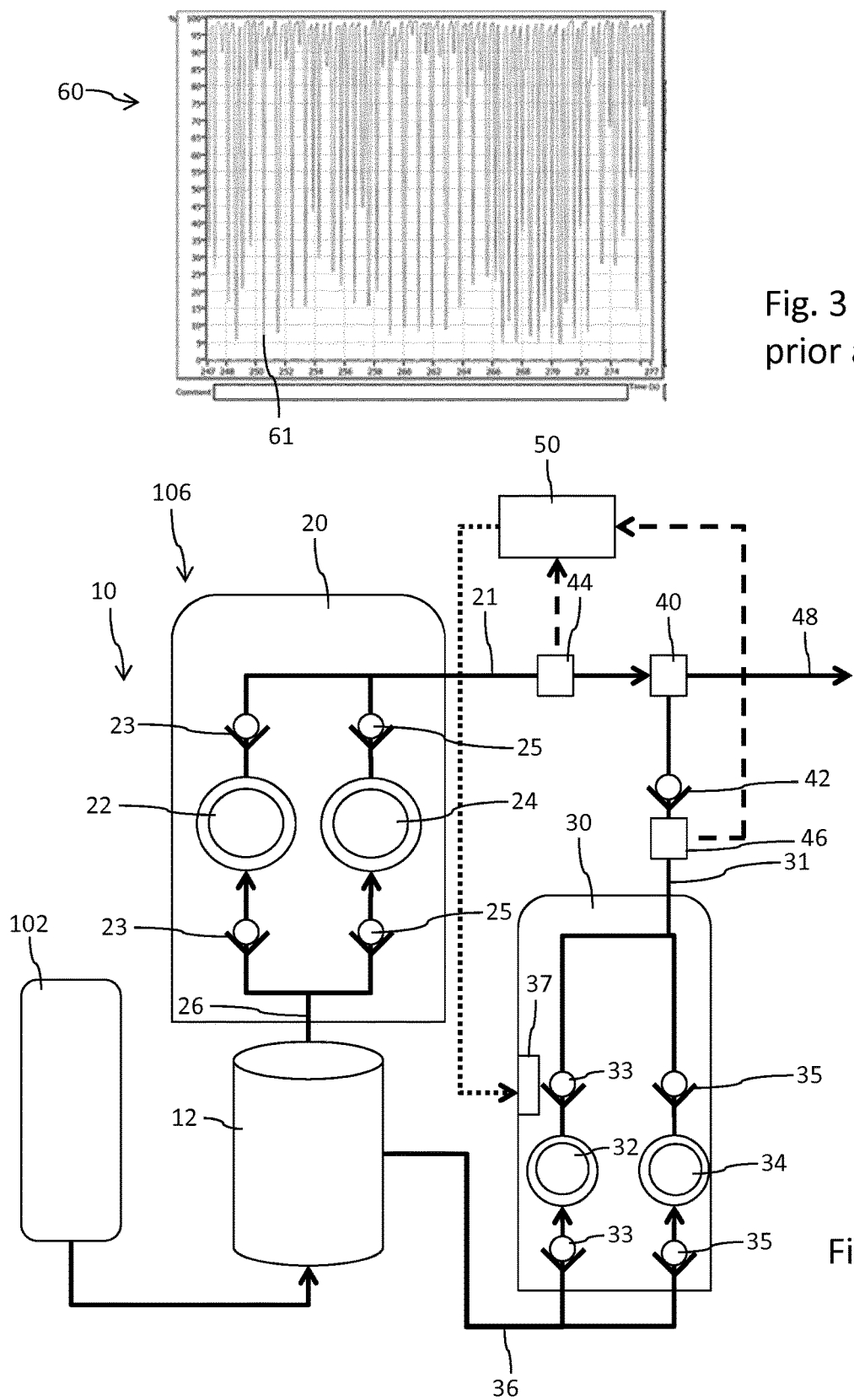
FIG. 3 shows a diagram of the flow volume of the pump over time according to the prior art.
FIG. 4 shows an embodiment of a pumping system according to the present invention.

The pumping system 10 as illustrated in FIG. 4 comprises two pumps, namely a first pump 20 and a second pump 30. First and second pumps 20, 30 are arranged in parallel. The first pump 20 comprises a first pump inlet 26 which is in direct fluid communication with a storage reservoir 102 containing the fluid to be pressurized by the pumping system 10. Between the storage reservoir 102 and first and second pumps 20, 30 there is located a cooler 12 in order to pre-cool the liquid to a predetermined temperature. The pump 20 may be identical to the pump 20 as known in the prior art and as for instance illustrated in FIG. 2. In the present embodiment the pump 20 is a duplex pump featuring two pump heads 22, 24. Typically, the pump heads 22, 24 are cooled in order to counteract heating of the pump 20 when in operation.

The second pump 30 acting as a dosing or auxiliary pump also comprises a duplex pump with two pump heads 32, 34. Likewise the first pump 20 the second pump 30 also comprises check valves 33 downstream and upstream of the pump head 32 and further comprises check valves 35 downstream and upstream of the pump head 34. The duplex pump design requires that the pump heads 32, 34 are connected in parallel. The second pump 30 also comprises a second pump inlet 36 which is parallel to the first pump inlet 26 of the first pump 20. As illustrated in FIG. 4, the first pump inlet 26, i.e. the inlet of the first pump 20 and the second pump inlet 36, i.e. the pump inlet 36 of the second pump 30 are individually connected and are both in fluid communication with the cooler 12 and/or with the storage reservoir 102. Alternatively it is conceivable, that first and second pump inlets 26, 36 are independently connected to the storage reservoir 102.

The pumping system 10 further comprises a junction 40, which in the present embodiment is designed as a T-junction. In this way a first pump outlet 21, i.e. the outlet 21 of the first pump 20 and a second pump outlet 31, i.e. the outlet 31 of the second pump 30, merge in the junction 40. The fluid flows provided by first and second pump outlets 21, 31 merge by way of the junction 40 and are both guided to a main outlet 48 which enters the chromatography system 100 as illustrated in FIG. 1. The pumping system 10 as shown in FIG. 4 may be integrated in at least one of the preparation stages 106, 108. It is also conceivable, that the pumping system 10 is integrated in both preparation stages 106, 108 of the chromatography system 100.

The pumping system 10 as shown in FIG. 4 also comprises a control 50 to regulate the second pump's 30 second output pressure p2 on the basis of a measurement of the first pump's 20 output pressure p1. In order to control and to measure output pressures p2, p1 there are provided two pressure sensors 44, 46 in the first and second pump outlets 21, 31 respectively. A first pressure sensor 44 is arranged in the fluid path of the first pump outlet 21 upstream of the junction 40 but downstream of the first pump 20. By means of the first pressure sensor 44 the output pressure p1 of the first pump 20 is detectable and/or quantitatively measurable. In the absence of the second pump 30 the output pressure p1 behaves in a similar way as the flow volume as illustrated in the diagram 60 of FIG. 3. Hence, the output pressure is subject to periodic or frequent significant drops 61.

In the fluid path of the second pump 30, hence in or downstream of the second pump outlet 31 but upstream of the junction 40 there is provided a check valve 42. The check valve 42 not only prevents backflow of pressurized fluid into the second pump outlet 31 towards the second pump 30 but provides an effective means that the regular feed flow pulsations 61 of the output stream of the first pump outlet 21 are substantially compensated.

In the event that the first output pressure p1 drops below a predefined threshold the check valve 42 at least temporally opens so that an auxiliary fluid flow emanating from the second pump 30 enters the junction 40 and contributes to the main output stream flowing to and through the main outlet 48 downstream of the junction 40. If the pressure in the first pump outlet 21 rises back to a predefined and normal level the momentary pressure difference p1-p2 between the first pump outlet 21 and the second pump outlet 31 drops below a predefined threshold. As a consequence the check valve 42 closes.

The check valve 42 may be implemented in many different ways. It may be spring biased and may be hence completely mechanically implemented. It is also conceivable, that the check valve 42 is implemented as an electromechanical or as a magnetic valve which is electrically controllable, e.g. by the control 50.

As already mentioned, there is also provided a second pressure sensor 46 in or at the second pump outlet 31. The second pressure sensor 46 is typically arranged upstream of the check valve 42 and hence upstream of the junction 40. By means of the second pressure sensor 46 the second output pressure p2 provided by the second pump 30 can be measured. Since first and second pressure sensors 44, 46 are both connected to the control 50, the control 50 is operable to determine and to monitor a pressure difference p1-p2 between first and second pump outlets 21, 31.

Moreover, the control 50 is connected to a drive 37 of the second pump 30. In this way, the output pressure, hence the second output pressure p2 can be adjusted and regulated by the control 50. By measuring the first output pressure p1 by means of the first pressure sensor 44 and by measuring the second output pressure p2 by means of the second pressure sensor 46 the control 50 is operable to keep the second output pressure p2 at least slightly below the pressure level of the first output pressure p1. In this way the operation of the second pump p2 effectively serves to compensate feed flow pulsations but since the pressure level of the second output pressure p2 is always below the predefined level of the first output pressure p1 the total pressure at the main outlet 48 will not exceed a predefined pressure level of the first pump 21.

Typically, the pressure difference between first output pressure p1 and second output pressure p2 is regulated to be in a range between 0.25% and 2.5% of the first output pressure p1.

Figure 5:
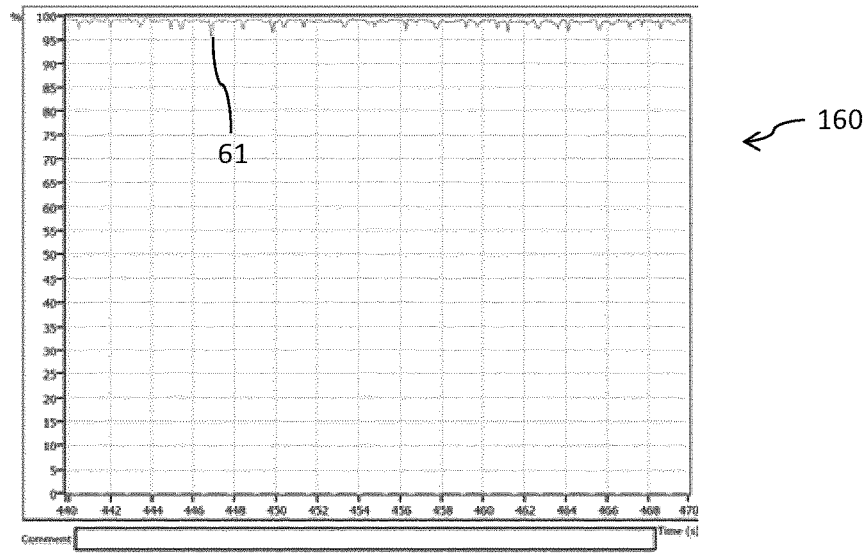
FIG. 5 shows a diagram of the flow volume over time of the pumping system according to FIG. 4

From a comparison of the diagram 160 of FIG. 5 with the diagram 60 of FIG. 3 it is immediately apparent, that implementation and use of the second pump 30 in parallel with the first pump 20 immediately reduces feed flow pulsations and pressure drops or flow volume drops 61 in the flow of the main outlet 48. As can be seen from the diagram 160 of FIG. 5, the flow volume over time exhibits rather small drops 161 or ripples that are typically less than 1%-5% of the total level of the flow volume or of the pressure level of the first output pressure p1.

Figure 6:
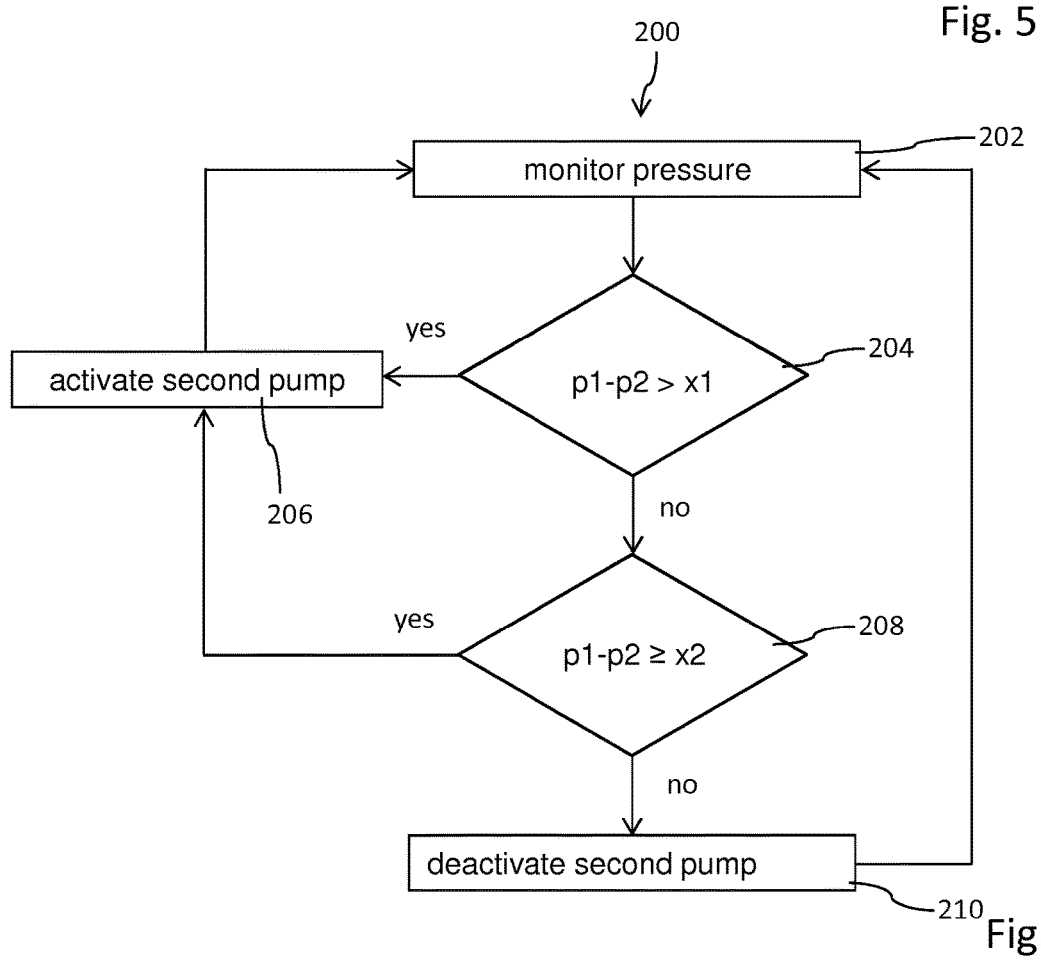
FIG. 6 shows a flowchart of the method of operating the pumping system according to FIG. 4.

The flowchart 200 according to FIG. 6 shows a rather simplified scheme of the implementation of the method for operating the pumping system 10. In a first step 202 at least the second output pressure p2 of the second pump 30 is monitored and measured. In a proceeding step 204 the measured second output pressure p2 is compared with either a predefined and constant first output pressure p1 of the first pump 20. It may also be compared with a first pressure p1 which is actually measured by a first pressure sensor 44 in the first outlet 31. In the event that the pressure difference p1-p2 between first output pressure p1 and second output pressure p2 is above a given upper threshold x1 in a next step 206 the second pump 30 will be activated. As a consequence the second output pressure p2 rises which will be measured in step 202. If the pressure difference p1-p2 is still too large the loop of steps 202, 204, 206 continues until it is determined in step 204 that the pressure difference between first and second output pressures p1, p2 is smaller than x1 but larger than x2 defining a lower threshold of the difference between p1 and p2.

Then the method continues with step 208, where the second output pressure p2 is again compared with the first output pressure p1. But here and in contrast to step 204 it is controlled and determined whether the difference between output pressures p1 and p2 is above a given minimum threshold x2. Typically, the pressure difference between output pressures p1 and p2 should be larger than 1 bar or should be larger than 0.25% of the first output pressure p1. In other words, in step 208 a check is performed that the second output pressure p2 is at least 1 bar less than the first output pressure p1.

In the event that it is determined in step 208 that the second output pressure p2 approaches the minimum difference to the first output pressure p1 then in step 210 the second pump 30 is deactivated.

As long as the second output pressure p2 is within a predefined difference to the first output pressure p1, hence as long as the difference p1-p2 is larger than x2 but smaller than x1 the method continues with the loop of steps 202, 204, 208 and 206. In the event that the second output pressure p2 approaches the first output pressure p1, hence that the difference between first and second output pressures p1, p2 drops below a predefined minimum difference x2 the second pump 30 will be deactivated in step 210.

Instead of activating or deactivating the second pump 30 it is also generally conceivable that pump power or pump capacity of the second pump 30 is regulated accordingly.

LIST OF REFERENCE NUMERALS 10 pumping system
12 cooler 20 first pump
21 pump outlet
22 pump head
23 check valve
24 pump head
25 check valve
26 pump inlet
30 second pump
31 pump outlet
32 pump head
33 check valve
34 pump head
35 check valve
36 pump inlet
37 drive
40 junction
42 check valve
44 pressure sensor
46 pressures sensor
48 main outlet
50 control
60 diagram
61 drop
100 chromatography system
102 storage reservoir
104 storage reservoir
106 preparation stage
108 preparation stage
109 probe injector
110 chromatography column
112 UV-detector
114 spectrometer
116 back-pressure regulator
118 heat exchanger
119 liquid gas separator
120 fraction collector
122 main fractions
160 diagram
161 drop

The invention claimed is:

1. A pumping system for compressible fluids, the pumping system comprising:
 a first pump having a first pump outlet,
 a second pump having a second pump outlet, the second pump arranged in parallel with the first pump, wherein the first pump outlet and the second pump outlet merge in a junction which is in fluid communication with a main outlet; and
 a controller to regulate an output pressure of the second pump on the basis of a measurement of an output pressure of the first pump such that the output pressure of the second pump is kept below the output pressure of the first pump and wherein a maximum flow volume of the second pump is less than 20% of a maximum flow volume of the first pump.

2. The pumping system according to claim 1, wherein at least one check valve is arranged between the junction and the second pump outlet.

3. The pumping system according to claim 1, wherein the first pump comprises a first pump inlet and the second pump comprises a second pump inlet, wherein first and second pump inlets are connectable in parallel with a storage reservoir at least partially filled with the compressible fluid.

4. The pumping system according to claim 1, wherein the controller is operable to adjust the output pressure of the second pump below the output pressure of the first pump.

5. The pumping system according to claim 4, wherein the controller is operable to adjust the output pressure of the second pump to a level which is from 1 bar to 10bar below the output pressure of the first pump.

6. The pumping system according to claim 1, further comprising a first pressure sensor connected to the controller and being in flow communication with the first outlet upstream of the junction.

7. The pumping system according to claim 1, further comprising a second pressure sensor connected to the controller and being in flow communication with the second outlet upstream of the junction.

8. The pumping system according to claim 1, wherein the controller is configured to drive the first and second pumps asynchronously.

9. A chromatography system comprising:
 at least one storage reservoir for storing and/or preparing at least one solvent; and
 a pumping system comprising
 a first pump having a first pump outlet,
 a second pump having a second pump outlet, the second pump arranged in parallel with the first pump, wherein the first pump outlet and the second pump outlet merge in a junction which is in fluid communication with a main outlet, and
 a controller to regulate an output pressure of the second pump on the basis of a measurement of an output pressure of the first pump such that the output pressure of the second pump is kept below the output pressure of the first pump, wherein a maximum flow volume of the second pump is less than 20% of a maximum flow volume of the first pump; and
 at least one detection or analyzing unit to analyze a substance extracted by the solvent.

10. The chromatography system according to claim 9, wherein the first pump comprises a first pump inlet and the second pump comprises a second pump inlet, the first and second pump inlets being connectable in parallel with the at least one storage reservoir.

11. The chromatography system according to claim 9, wherein the chromatography system is in the form of a supercritical fluid chromatography system, wherein the pumping system is operable to feed pressurized CO2.

12. A method of operating a pumping system, the method comprising:
 measuring an output pressure at a pump outlet of a first pump, the first pump arranged parallel with a second pump;
 adjusting an output pressure at a pump outlet of the second pump on the basis of the measured output pressure at the pump outlet of the first pump such that the output pressure of the second pump is kept below the output pressure of the first pump; and
 deactivating the second pump or reducing at least one of a pump power and a pump capacity of the second pump when a difference between the output pressure of the second pump and the output pressure of the first pump drops below a predefined minimum difference.

13. The method according to claim 12, wherein the predefined minimum difference is between about 1 bar and 10 bar.

14. The method according to claim 12, further comprising operating the first pump and the second pump such that a fluid flow from the pump outlet of the first pump and a fluid flow from the pump outlet of the second pump are merged and guided to a chromatography system.

15. The method according to claim 14, further comprising detecting a drop in the output pressure at the pump outlet of the first pump, wherein adjusting the output pressure at the pump outlet of the second pump comprises adjusting the output pressure at the pump outlet of the second pump based on the detected drop.

16. The method according to claim 12, further comprising driving the first pump and the second pump asynchronously.

17. A method of operating a pumping system, the method comprising:
    measuring an output pressure at a pump outlet of a first pump;
    adjusting an output pressure at a pump outlet of a second pump on the basis of the measured output pressure at the pump outlet of the first pump, wherein adjusting the output pressure at the pump outlet of the second pump comprises maintaining the output pressure at the pump outlet of the second pump below the output pressure at the pump outlet of the first pump by a predefined minimum difference; and
    deactivating the second pump or reducing at least one of a pump power and a pump capacity of the second pump when a difference between the output pressure of the second pump and the output pressure of the first pump drops below the predefined minimum difference.

18. A pumping system for compressible fluids, the pumping system comprising:
    a first pump having a first pump outlet;
    a second pump having a second pump outlet, the second pump arranged in parallel with the first pump, wherein the first pump outlet and the second pump outlet merge in a junction which is in fluid communication with a main outlet; and
    a controller to regulate an output pressure of the second pump on the basis of a measurement of an output pressure of the first pump such that the output pressure of the second pump is kept below the output pressure of the first pump, wherein the controller is operable to deactivate the second pump or to reduce at least one of a pump power and a pump capacity of the second pump when a difference between the output pressure of the second pump and the output pressure of the first pump drops below a predefined minimum difference.

19. A chromatography system comprising:
    at least one storage reservoir for storing and/or preparing at least one solvent;
    a pumping system comprising:
        a first pump having a first pump outlet;
        a second pump having a second pump outlet, the second pump arranged in parallel with the first pump, wherein the first pump outlet and the second pump outlet merge in a junction which is in fluid communication with a main outlet; and
        a controller to regulate an output pressure of the second pump on the basis of a measurement of an output pressure of the first pump such that the output pressure of the second pump is kept below the output pressure of the first pump, wherein the controller is operable to deactivate the second pump or to reduce at least one of a pump power and a pump capacity of the second pump when a difference between the output pressure of the second pump and the output pressure of the first pump drops below a predefined minimum difference; and
    at least one detection or analyzing unit to analyze a substance extracted by the solvent.

* * * * *